US012616394B2

(12) United States Patent
Kang et al.

(10) Patent No.: US 12,616,394 B2
(45) Date of Patent: May 5, 2026

(54) APPARATUS AND METHOD FOR USER RECOGNITION BASED ON OXYGEN SATURATION

(71) Applicant: SAMSUNG ELECTRONICS CO., LTD., Suwon-si (KR)

(72) Inventors: Jae Min Kang, Suwon-si (KR); Byung Hoon Ko, Suwon-si (KR); Seung Woo Noh, Suwon-si (KR); Sang Yun Park, Suwon-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 497 days.

(21) Appl. No.: 18/129,427

(22) Filed: Mar. 31, 2023

(65) Prior Publication Data

US 2024/0188852 A1     Jun. 13, 2024

(30) Foreign Application Priority Data

Dec. 13, 2022    (KR) ........................ 10-2022-0173989

(51) Int. Cl.
*A61B 5/00*       (2006.01)
*A61B 5/0205*     (2006.01)
*A61B 5/117*      (2016.01)
*A61B 5/021*      (2006.01)

(52) U.S. Cl.
CPC ............ *A61B 5/117* (2013.01); *A61B 5/0205* (2013.01); *A61B 5/02108* (2013.01)

(58) Field of Classification Search
CPC ............................... A61B 5/117; A61B 5/0205
See application file for complete search history.

(56) References Cited

U.S. PATENT DOCUMENTS

| | | | | | |
|---|---|---|---|---|---|
| 5,719,950 | A | * | 2/1998 | Osten ...................... | G06V 40/40 |
| | | | | | 340/5.82 |
| 9,042,971 | B2 | * | 5/2015 | Brumback .............. | H04L 67/12 |
| | | | | | 600/595 |
| 9,558,336 | B2 | * | 1/2017 | Lee ......................... | A61B 5/349 |
| 9,693,711 | B2 | * | 7/2017 | Yuen ....................... | G01P 13/00 |
| 9,721,409 | B2 | | 8/2017 | Sezan et al. | |

(Continued)

FOREIGN PATENT DOCUMENTS

| | | | | |
|---|---|---|---|---|
| JP | 6785611 | B2 | * 11/2020 | ........... A61B 5/1172 |
| KR | 10-1183160 | B1 | 9/2012 | |

(Continued)

OTHER PUBLICATIONS

JP 6785611 B2 English Translation from Google Patents (Year: 2016).*

(Continued)

*Primary Examiner* — Shirley X Jian
(74) *Attorney, Agent, or Firm* — Sughrue Mion, PLLC

(57) ABSTRACT

An apparatus for performing user recognition may include: a first sensor configured to measure health information from a user; a second sensor configured to measure a pulse wave signal from the user; and a processor configured to obtain oxygen saturation based on the pulse wave signal, to recognize the user based on an oxygen saturation pattern of the obtained oxygen saturation, and to update the measured health information as health information of the recognized user.

16 Claims, 16 Drawing Sheets

(56)  References Cited

U.S. PATENT DOCUMENTS

| | | | | |
|---|---|---|---|---|
| 9,851,808 | B2 * | 12/2017 | Yuen | A61B 5/1123 |
| 10,025,917 | B2 | 7/2018 | Sezan et al. | |
| 10,126,830 | B2 * | 11/2018 | Yuen | A61B 5/7264 |
| 10,318,832 | B2 * | 6/2019 | Shin | G06F 21/32 |
| 10,503,268 | B2 * | 12/2019 | Yuen | A61B 5/725 |
| 10,617,357 | B2 * | 4/2020 | Miller | G16H 40/67 |
| 10,687,717 | B1 * | 6/2020 | Peterson | A61B 5/14551 |
| 10,888,280 | B2 * | 1/2021 | Newberry | A61B 5/7264 |
| 10,942,579 | B2 * | 3/2021 | Yuen | A61B 5/742 |
| 10,973,446 | B2 * | 4/2021 | Schie | G01N 33/49 |
| 11,070,550 | B2 * | 7/2021 | Rahmel | H04W 12/33 |
| 11,096,048 | B2 * | 8/2021 | Li | H04W 12/69 |
| 11,291,401 | B2 * | 4/2022 | Velo | G06N 20/00 |
| 11,419,529 | B2 | 8/2022 | Choi et al. | |
| 11,451,536 | B2 * | 9/2022 | MacLean | H04L 63/0853 |
| 11,593,469 | B2 * | 2/2023 | Bannerjee | H04L 9/12 |
| 11,627,887 | B2 * | 4/2023 | Peterson | A61B 5/02438 |
| | | | | 600/478 |
| 11,720,656 | B2 * | 8/2023 | Oung | G06F 21/32 |
| | | | | 713/186 |
| 11,883,167 | B2 * | 1/2024 | Schie | A61B 5/7207 |
| 11,903,680 | B2 * | 2/2024 | Frank | A61B 5/1455 |
| 12,193,792 | B2 * | 1/2025 | Frank | A61B 5/165 |
| 12,232,850 | B2 * | 2/2025 | Frank | A61B 5/7282 |
| 12,257,075 | B2 * | 3/2025 | Miller | G16H 50/30 |
| 12,293,844 | B2 * | 5/2025 | Frank | A61B 5/02055 |
| 2015/0135310 | A1 * | 5/2015 | Lee | G06F 1/163 |
| | | | | 726/20 |
| 2016/0051191 | A1 * | 2/2016 | Miller | A61B 5/0205 |
| | | | | 600/300 |
| 2017/0039358 | A1 * | 2/2017 | Yuen | A61B 5/7267 |
| 2019/0188365 | A1 * | 6/2019 | Gurin | G06F 21/32 |
| 2020/0085315 | A1 | 3/2020 | Kang et al. | |
| 2020/0205731 | A1 * | 7/2020 | Miller | G16H 50/30 |
| 2021/0068668 | A1 * | 3/2021 | Slyusarenko | A61B 5/7235 |
| 2021/0303668 | A1 * | 9/2021 | Bannerjee | A61B 5/117 |
| 2024/0188852 | A1 * | 6/2024 | Kang | A61B 5/0205 |
| 2025/0213189 | A1 * | 7/2025 | Miller | G16H 20/30 |

FOREIGN PATENT DOCUMENTS

| | | | | | |
|---|---|---|---|---|---|
| KR | 10-1793587 | B1 | 11/2017 | | |
| KR | 10-2020-0091625 | A | 7/2020 | | |
| KR | 10-2146089 | B1 | 8/2020 | | |
| KR | 102278410 | B1 * | 7/2021 | | A61B 5/02108 |
| KR | 10-2336489 | B1 | 12/2021 | | |

OTHER PUBLICATIONS

KR 102278410 B1 English Translation from Google Patents (Year: 2020).*

* cited by examiner

Figure 6C:
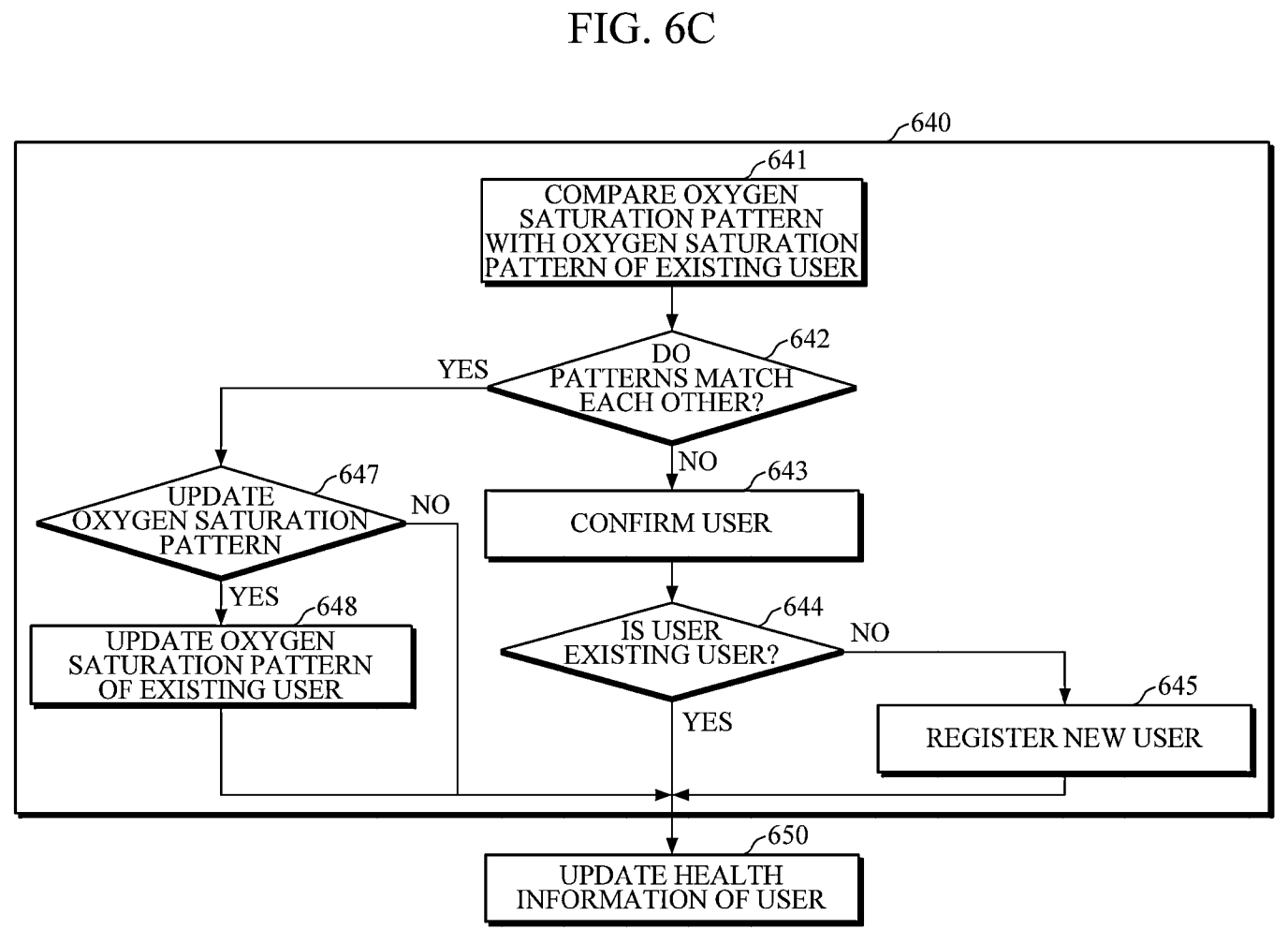

COMPARE OXYGEN SATURATION PATTERN WITH OXYGEN SATURATION PATTERN OF EXISTING USER

642

DO PATTERNS MATCH EACH OTHER?

YES

NO

643

CONFIRM USER

644

IS USER EXISTING USER?

NO

YES

645

REGISTER NEW USER

647

UPDATE OXYGEN SATURATION PATTERN

NO

YES

648

UPDATE OXYGEN SATURATION PATTERN OF EXISTING USER

650

UPDATE HEALTH INFORMATION OF USER

APPARATUS AND METHOD FOR USER RECOGNITION BASED ON OXYGEN SATURATION

CROSS-REFERENCE TO RELATED APPLICATION(S)

This application claims priority from Korean Patent Application No. 10-2022-0173989, filed on Dec. 13, 2022, in the Korean Intellectual Property Office, the disclosure of which is incorporated herein by reference in its entirety.

BACKGROUND

1. Field

Apparatuses and methods consistent with example embodiments relate to recognizing users based on oxygen saturation and performing health information management.

2. Description of the Related Art

Recently, electronic devices such as smartwatches have incorporated technology for measuring various health data, including electrocardiogram, body fat, blood glucose, and blood pressure. As health data contains sensitive personal information, accurately matching the measured health data to users may be necessary to control measurement of health information and ensure proper medical information management. Cross-contamination of health information between patients may pose a serious risk to the patients. Authentication methods such an iris sensor, a fingerprint sensor, and the like may be used to authenticate users to ensure that only the intended user can access his or her health data. However, these authentication processes may be inconvenient, and mounting additional sensors may be challenging.

SUMMARY

According to an aspect of the present disclosure, an apparatus for performing user recognition, may include: a first sensor configured to measure health information from a user; a second sensor configured to measure a pulse wave signal from the user; and a processor configured to obtain oxygen saturation based on the pulse wave signal, recognize the user based on an oxygen saturation pattern of the obtained oxygen saturation, and update the measured health information as health information of the recognized user.

The second sensor may include a light source configured to emit light of multiple wavelengths to skin of the user, and a detector configured to detect the light reflected or scattered from the user.

The second sensor may include a plurality of channels, wherein each of the plurality of channels has at least one light source and at least one detector.

The processor may be further configured to calculate the oxygen saturation at each time point in a predetermined period of the pulse wave signal, and generate the oxygen saturation pattern of the user based on a statistical value of the oxygen saturation calculated at each time point.

The apparatus may include a storage configured to store oxygen saturation patterns of one or more existing users, wherein the processor may be further configured to recognize, as the user, an existing user that matches the oxygen saturation pattern of the user among the oxygen saturation patterns of the one or more existing users.

In response to no oxygen saturation pattern in the storage matching the oxygen saturation pattern of the user, the processor may be further configured to recognize the user based on an input of the user.

In response to the user being a new user, the processor may be configured to register the new user in the storage, and store the measured health information as health information of the new user.

The processor may be further configured to calculate a similarity between the oxygen saturation pattern of the user and an oxygen saturation pattern of an existing user that is stored in a storage, and in response to the similarity being greater than or equal to a first threshold value, the processor is configured to determine that the oxygen saturation pattern of the user matches the oxygen saturation pattern of the existing user.

In response to the similarity between the oxygen saturation pattern of the user and the oxygen saturation pattern of the existing user, being greater than or equal to the first threshold value, and being less than or equal to a second threshold value, the processor may be further configured to update the oxygen saturation pattern of the existing user based on the oxygen saturation pattern of the user.

The apparatus may include a storage configured to store user information, including one or more of height, weight, age, gender, and health information of one or more existing users, wherein the first sensor may be further configured to extract the user information of the recognized user from the storage, and obtain the health information based on the extracted user information.

The health information may include one or more of electrocardiogram, blood glucose, body fat, body mass, blood pressure, heart rate, body temperature, triglyceride, and antioxidant index.

According to another aspect of the present disclosure, a method of performing user recognition may include: measuring health information from a user; measuring a pulse wave signal from the user; obtaining oxygen saturation based on the pulse wave signal; recognizing the user based on an oxygen saturation pattern of the user; and updating the measured health information as health information of the recognized user.

The obtaining of the oxygen saturation may include: calculating the oxygen saturation at each time point in a predetermined period of the pulse wave signal; and generating the oxygen saturation pattern of the user based on a statistical value of the oxygen saturation calculated at each time point.

The recognizing of the user may include recognizing, as the user, an existing user that matches the oxygen saturation pattern of the user, among oxygen saturation patterns of one or more existing users which are stored in a storage.

The recognizing of the user may include, in response to no oxygen saturation pattern in the storage matching the oxygen saturation pattern of the user, recognizing the user based on an input of the user.

The method may further include, in response to the user being a new user, registering the new user in the storage, wherein the updating of the measured health information may include storing the measured health information as health information of the new user.

The recognizing of the user may include: calculating a similarity between the oxygen saturation pattern of the user and an oxygen saturation pattern of an existing user; and in response to the similarity being greater than or equal to a first threshold value, determining that the oxygen saturation pattern of the user matches the oxygen saturation pattern of the existing user.

The recognizing of the user may include, in response to the similarity between the oxygen saturation pattern of the user and the oxygen saturation pattern of the existing user being greater than or equal to the first threshold value, and being less than or equal to a second threshold value, updating the oxygen saturation pattern of the existing user based on the oxygen saturation pattern of the user.

The method may include extracting user information of the recognized user from the storage, wherein the measuring of the health information may include obtaining the health information based on the extracted user information.

According to another aspect of the present disclosure, an electronic device may include: a photoplethysmogram (PPG) sensor configured to measure a pulse wave signal from a user; a memory configured to store one or more instructions; and a processor configured to execute the one or more instructions to: obtain oxygen saturation based on the pulse wave signal; recognize the user based on an oxygen saturation pattern of the oxygen saturation; and control an operation of the electronic device or another device connected to the electronic device based on a recognition of the user.

BRIEF DESCRIPTION OF THE DRAWINGS

The above and/or other aspects will be more apparent by describing certain example embodiments, with reference to the accompanying drawings, in which:

FIGS. 6B and 6C are diagrams illustrating examples of a user recognition operation;

DETAILED DESCRIPTION

Figure 1:
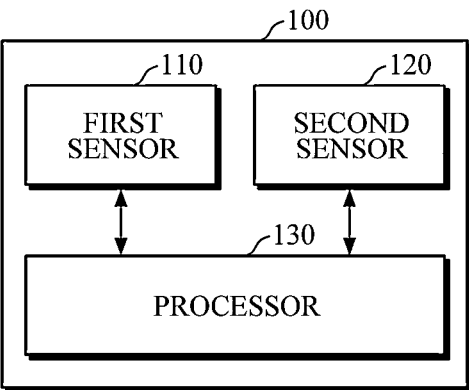
FIG. 1 is a block diagram illustrating an apparatus for user recognition according to an embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms "first," "second," etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

FIG. 1 is a block diagram illustrating an apparatus for user recognition according to an embodiment of the present disclosure.

Referring to FIG. 1, an apparatus 100 for user recognition (hereinafter referred to as a user recognition apparatus) includes a first sensor 110, a second sensor 120, and one or more processors 130.

The first sensor 110, the second sensor 120, and the one or more processors 130 may be implemented in a single hardware device, or at least some of the components may be implemented in another hardware device which is physically separated. At least some functions of the first sensor 110, the second sensor 120, or the processor 130 may be performed by other components. For example, the second sensor 120 may be one of sensors included in the first sensor 110. At least some of the one or more processors 130 may perform the function of measuring health information in conjunction with the first sensor 110.

The first sensor 110 may measure health information from a user. The health information may include information related to a user's health and/or information related to a user's activities, and the like. The health-related information may include blood pressure, antioxidant index, blood glucose, triglyceride, calories, heart rate, body temperature, body water, body fat, body mass, electrocardiogram, arterial stiffness, skin age, photoplethysmogram (PPG), bioelectrical impedance analysis (BIA), electrocardiogra (ECG), electromyography (EMG), impedance plethysmogram (IPG), Pressure wave, video plethysmogram (VPG), etc., and the activity-related information may include current position, amount of exercise, activity time, step count, movement distance, movement speed, stress, sleep information (sleep time, sleep stages, sleep quality), and the like.

The first sensor 110 may include one or more sensors for measuring the health information. The one or more sensors may include Global Positioning System (GPS), gesture sensor, gyro sensor, barometric pressure sensor, magnetic sensor, acceleration sensor, grip sensor, proximity sensor, color sensor, infrared (IR) sensor, compass sensor, step counter sensor, ultraviolet sensor, 3D touch sensor, biosensor, body temperature sensor, temperature sensor, humidity sensor, and/or illuminance sensor, and the like. The biosensor is a sensor for measuring the above health-related information, and examples thereof may include PPG sensor, BIA sensor, ECG sensor, GMG sensor, IPG sensor, VPG sensor, spectrometer, and the like.

The second sensor 120 may measure a pulse wave signal from a user. The second sensor 120 may be a photoplethysmogram (PPG) sensor configured to measure a PPG signal. the second sensor 110 may include a light source configured to emit light to the user's skin, and a detector configured to detect light returning after scattering or reflection from or transmission into the skin surface of the user or body tissue such as blood vessels and the like. The second sensor 120 may include multiple channels, wherein each of the channels has at least one light source and at least one detector (e.g., a pair of a light source and a light detector, a set of a single light source and a plurality of detectors, a set of a plurality of light sources and a single detector, a set of a plurality of light sources and a plurality of detectors). The light source may emit light of at least two or more wavelengths including infrared and red wavelengths. The light source may include a light emitting diode (LED), a laser diode (LD), a phosphor, and the like. The detector may include a photo diode, a photo transistor (PTr), an image sensor (e.g., complementary metal-oxide semiconductor (CMOS) image sensor), and the like.

The processor 130 may establish a wired or wireless connection with the first sensor 110 and the second sensor 120, enabling the processor 130 to control the first sensor 110 and the second sensor 120. Upon a user requests health information measurement, the processor 130 may control the first sensor 110 to measure health information from the user, and before, after, or at the same time as the measurement of the health information, the processor 130 may control the second sensor 120 to measure a pulse wave signal from the user. A biosensor (e.g., PPG sensor) of the first sensor 110 may operate as the second sensor 120. For example, if a PPG sensor measures a PPG signal from a user to measure health information such as blood pressure and the like, the measured PPG signal may be used as the pulse wave signal of the second sensor 120.

The processor 130 may receive a user's health information and pulse wave signal from the first sensor 110 and the second sensor 120. The processor 130 may perform preprocessing, such as filtering to remove noise from the received pulse wave signal, amplifying the pulse wave signal, or converting the signal into a digital signal, and the like. Also, the processor 130 may correct the pulse wave signal by reconstructing the pulse wave signal based on Fast Fourier Transform. However, the preprocessing is not limited thereto, and various other preprocessing operations may be performed according to computing performance or measurement accuracy of the apparatus, the purpose of estimating oxygen saturation, measurement portion of a user, and various measurement environments, such as temperature and humidity of an object, temperature of a sensor, and the like.

The processor 130 may recognize a user whose which health information is measured, based on the pulse wave signal and may manage the measured health information as the recognized user's health information. The processor 130 may obtain oxygen saturation based on the pulse wave signal, may extract an oxygen saturation pattern from the obtained oxygen saturation, and may recognize a user based on the extracted oxygen saturation pattern. In this manner, even when the apparatus 100 is used by a plurality of users, the processor 130 may automatically recognize the users based on the pulse wave signal without requiring additional user recognition information, thereby preventing cross-contamination of heath data between users.

Figure 2:
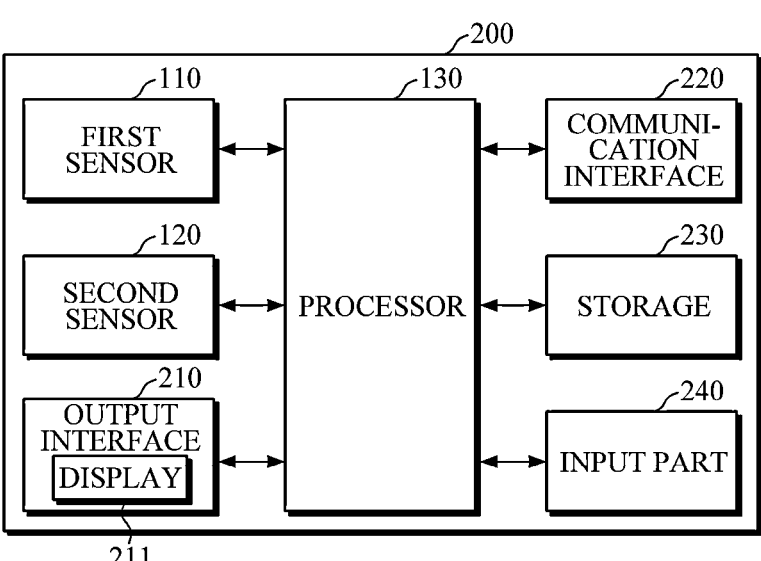
FIG. 2 is a block diagram illustrating an apparatus for user recognition according to another embodiment of the present disclosure.

FIG. 2 is a block diagram illustrating an apparatus for user recognition according to another embodiment of the present disclosure.

Referring to FIG. 2, the user recognition apparatus includes the first sensor 110, the second sensor 120, the processor 130, an output interface 210, a communication interface 220, a storage 230, and an input part 240. Some of the components may be omitted if necessary, and may also be included in another device which is physically separated. The first sensor 110, the second sensor 120, and the processor 130 are described above, such that the description thereof will be omitted below.

The output interface 210 may include a display 211, and in response to the processor 130 processing data, the output interface 210 may output the processed data to the display 210. For example, when the processor 130 recognizes a user, the output interface 210 may output user information and/or health information of the recognized user. The output interface 210 may further include an audio output module and/or a haptic module, etc., in addition to the display 211, and may output necessary information in a non-visual manner using sounds, vibrations, tactile sensation, and the like.

Under the control of the processor 130, the communication interface 220 may be connected to an external device by using wired and wireless communication techniques to transmit and receive various data. For example, in the case where the first sensor 110 and/or the second sensor 120 are included in separate hardware devices, the communication interface 220 may receive data from the first sensor 110 and/or the second sensor 120. Alternatively, the communication interface 220 may transmit data, measured by the first sensor 110 and/or the second sensor 120, to another device and may transmit a user recognition result of the processor 130 and/or a control signal for other device, which is generated by the processor 130, to the other device.

The wired and wireless communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, 3G, 4G, and 5G communications, and the like. However, the communication techniques are not limited thereto.

The storage 230 my store programs (application software) to be executed by the processor 130. The programs may include one or more instructions for performing various functions including the above operations of measuring the health information and recognizing users. In addition, the storage 230 may store a variety of information for user recognition which is to be referred to by the processor 130. The storage 230 may store a health information database (DB) for managing health information of registered existing users and a user DB for managing user information of the registered existing users. The user information may include personal information, such as a user's age, gender, height, weight, oxygen saturation pattern, and the like.

The storage 230 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The input part 230 may receive, from a user, instructions and/or data to be processed by the processor 120. The input part 230 may include a control button (e.g., stem of a smartwatch, volume/power button of a smartphone, etc.) of an electronic device (smartwatch, smartphone, etc.) including the user recognition apparatus 200, a touch screen of the display 211, a microphone, a mouse, a keyboard, a digital pen (stylus pen, etc.). The processor 130 may display a user interface on the display 211, and a user may input data, such as user information, through the user interface by using the input part 230.

Figure 3:
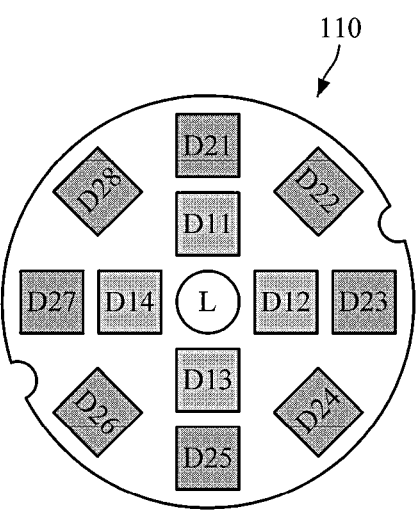
FIG. 3 is a diagram illustrating an example of a structure of a second sensor of an apparatus for user recognition.

FIG. 3 is a diagram illustrating an example of a structure of the second sensor of the user recognition apparatuses 100 and 200.

Referring to FIG. 3, the second sensor 120 may include a multi-wavelength light source L disposed at the center thereof. The multi-wavelength light source L may include two or more LEDs so as to emit light of at least two or more of infrared, red, green, and blue wavelengths. The second sensor 120 may include a plurality of channels, each of which may include at least one of detectors D11, D12, D13, D14, D21, D22, D23, D24, D25, D26, D27, and D28. The respective channels may be arranged around the light source L on a periphery thereof, with no limitation on the number of channels. The channels do not necessarily have a circular shape, and may be randomly disposed at an arbitrary position in a measurement region of the second sensor 120. Under the control of the processor 130, the light source L disposed at the center of the second sensor may be turned on in a time-division manner to sequentially emit light of each wavelength, while the plurality of channels may operate sequentially or simultaneously to detect light at different positions. For example, the plurality of channels may operate sequentially in a clockwise direction, counterclockwise direction, diagonal direction, etc. Alternatively, two or more channels may operate simultaneously.

However, the arrangement is not limited to the above example illustrated in FIG. 3, and one or more detectors may be disposed at the center, and the multi-wavelength light sources may be disposed in the plurality of channels. Alternatively, the multi-wavelength light source and one or more detectors may be disposed in each of the plurality of channels, and the plurality of channels may be operated sequentially or simultaneously in a predetermined pattern (clockwise direction, counterclockwise direction, diagonal direction, etc.). In this case, when a light source of a specific channel is driven, detectors of one or more channels at different positions may be driven.

Figure 4:
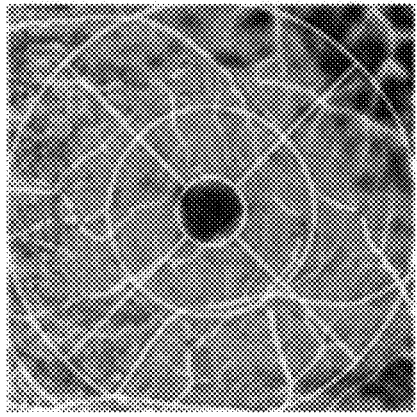
FIG. 4 is a diagram illustrating an example of a pattern in which a magnitude of an oxygen saturation signal, measured from a body surface by multiple channels, is mapped to a 2D image.

FIG. 4 is a diagram illustrating an example of a pattern in which a magnitude of an oxygen saturation signal, measured from a body surface by multiple channels, is mapped to a 2D image.

The processor 130 may estimate oxygen saturation based on a multi-wavelength pulse wave signal. For each channel, the processor 130 may extract a high-frequency band component and a low-frequency band component from a pulse wave signal at a first wavelength and a pulse wave signal at a second wavelength, respectively. The first wavelength and the second wavelength may be an infrared wavelength and a red wavelength, respectively. The processor 130 may extract the high-frequency band component by using a band-pass filter, and may extract the low-frequency band component by using a low-pass filter. The processor 130 may obtain the oxygen saturation for each channel by using the extracted high-frequency band component and low-frequency band component at each wavelength of the respective channels. A value of R may be calculated by the following Equations 1 to 5, and oxygen saturation SpO$_2$ may be obtained by applying the value of R to Equation 6.

$$R = \frac{F_1}{F_2} \qquad \text{[Equation 1]}$$

Herein, F$_1$ denotes a first feature value extracted from the pulse wave signal at the first wavelength, and F$_2$ denotes a second feature value extracted from the pulse wave signal at the second wavelength. For example, the first feature value and the second feature may be obtained using Equations 2 to 5, but are not limited thereto.

$$F_1 = \frac{(lp_1 - lv_1)}{lavg_1} \qquad \text{[Equation 2]}$$

$$F_2 = \frac{(lp_2 - lv_2)}{lavg_2}$$

$$F_1 = \ln\!\left(\frac{lp_1}{lv_1}\right) \qquad \text{[Equation 3]}$$

$$F_2 = \ln\!\left(\frac{lp_2}{lv_2}\right)$$

$$F_1 = \ln\!\left(\left(\frac{lp_1}{lv_1}\right)\Big/ lavg_1\right) \qquad \text{[Equation 4]}$$

$$F_2 = \ln\!\left(\left(\frac{lp_2}{lv_2}\right)\Big/ lavg_2\right)$$

$$F_1 = \ln((lp_1 - lv_1)/lavg_1) \qquad \text{[Equation 5]}$$

$$F_2 = \ln((lp_2 - lv_2)/lavg_2)$$

In Equations 2 to 4, $lp_1$, $lv_1$, $lp_2$, and $lv_2$ denote peak and valley values of the high-frequency band component of the pulse wave signal at each of the first wavelength and the second wavelength, and lavg1 and lavg2 denote low-frequency band component values at each of the first wavelength and the second wavelength, or an average of the peak and valley values.

$$SpO_2 = 110 - 25 \times R \qquad \text{[Equation 6]}$$

The processor 130 may obtain oxygen saturations at each time point in a predetermined time period (e.g., five seconds) of the pulse wave signal at the first wavelength and the pulse wave signal at the second wavelength for each channel, and may obtain, as oxygen saturation for each channel, a statistical value (e.g., average) of the oxygen saturations at each time point. As described above, upon obtaining the oxygen saturations for each channel, the processor 130 may create an oxygen saturation pattern map in the form of a contour line by mapping the oxygen saturations to their corresponding channel positions in the measurement region of the second sensor 120.

As described above, after generating the oxygen saturation pattern of a user, the processor 130 may compare the generated oxygen saturation pattern of the user with oxygen saturation patterns of existing users which are stored in the storage 230. If there is a matching existing user, the processor 130 may recognize the matching existing user as the user from which the health information is measured, and may update the measured health information as health information of the matching existing user in the health information DB.

In order to determine if the oxygen saturation patterns match, the processor 130 may calculate their similarity. For example, the processor 130 may calculate a similarity between the oxygen saturation pattern of the user, from which the health information is measured, with an oxygen saturation pattern of an existing user. If the similarity is greater than or equal to a first threshold value (e.g., 90%), the processor 130 may determine that the oxygen saturation patterns match each other. However, if the similarity is greater than or equal to the first threshold value, but is less than or equal to a second threshold value (e.g., 95%), the processor 130 may update the oxygen saturation pattern of the existing user by using the oxygen saturation pattern of the user. For example, the processor 130 may replace the oxygen saturation pattern of a recognized existing user with the oxygen saturation pattern of the user, or may generate a new oxygen saturation pattern by obtaining a statistical value (e.g., average) of the oxygen saturations for each of corresponding channels in both the oxygen saturation patterns, and may replace the oxygen saturation pattern of the existing user with the generated new oxygen saturation pattern.

If the processor 130 fails to match an existing user with the measured health information, the processor 130 may attempt to confirm the user's identity. As an way to confirm the user's identify, the processor 130 may display a user interface on the display 211 and may notify the user of the recognition failure. The processor 130 may recognize the user by allowing the user to select an existing user, or register a new user by inputting the user information. Alternatively, the processor 130 may inform the user of the recognition failure by transmitting a text message or a social media to the user's phone number or social media account stored in the storage 230. The messages may include a link that allows the user to designate an existing user or register him or her as a new user.

After the processor 130 recognizes the user, the first sensor 110 may extract user information such as height, weight, age, and/or gender of the recognized user by referring to the information stored the storage 230, and may finally measure health information (e.g., body fat) by using the user information which is required during calculation of health information.

FIGS. 5A to 5D are diagrams illustrating an example of a smartwatch electronic device including an apparatus for user recognition. The user recognition apparatuses 100 and 200 may be implemented in various electronic devices, such as a smart band, an ear-type electronic device, a smartphone, a tablet PC, a laptop computer, a desktop computer, etc., in addition to a smartwatch 500.

Figure 5A:
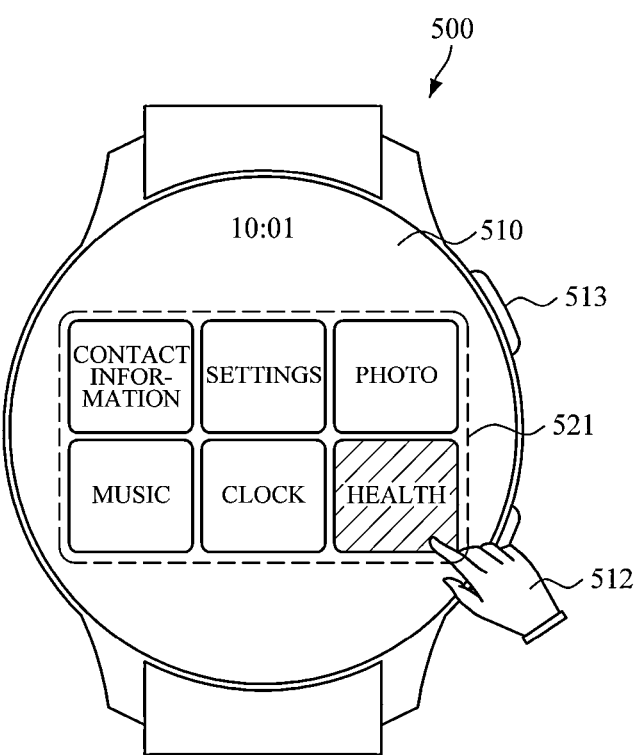
FIGS. 5A to 5D are diagrams illustrating an example of a smartwatch electronic device including an apparatus for user recognition.
Figure 5B:
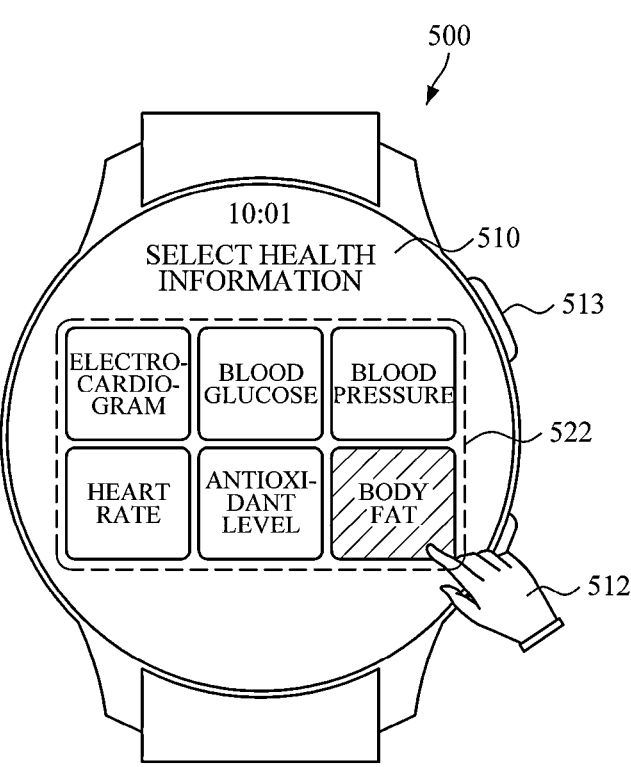
Figure 5C:
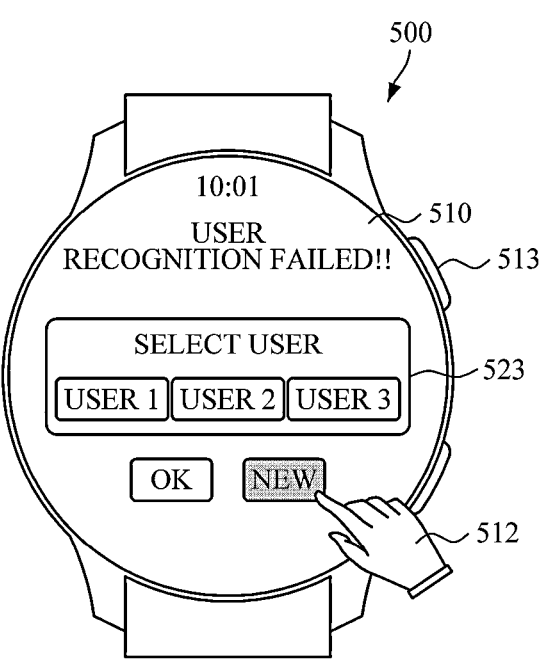

A user may transmit a request for measuring health information by running a health application using input parts 512 and 513 on a user interface 510 displayed on the smartwatch 500. Upon receiving the user's request through the input parts 512 and 513, the processor (e.g., the processor 130 of FIGS. 1 and 2) may display a health information list 522 to be measured on the user interface 510 as illustrated in FIG. 5B, and may control the first sensor (e.g., the first sensor 110 of FIGS. 1 and 2) to measure health information (e.g., body fat) selected by the user via the input parts 512 and 513. The first sensor may be disposed on a rear surface of a main body of the smartwatch 500. The input part 513 disposed on a side may also perform the function of the first sensor.

The processor (e.g., the processor 130 of FIGS. 1 and 2) may control the second sensor (e.g., the second sensor 120 of FIGS. 1 and 2) to measure a PPG signal from a user. In this case, the second sensor may be disposed on the rear surface of the main body of the smartwatch 500, and the input part 513 disposed on the side may also perform the function of the second sensor.

Figure 5D:
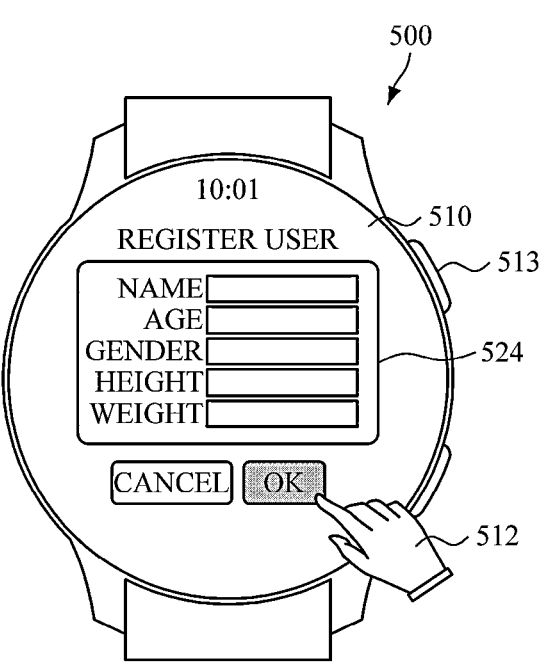

If user recognition is failed, the processor (e.g., the processor 130 of FIGS. 1 and 2) may display a message, such as "user recognition failed!!," on the user interface 510. The processor may extract existing user information from the storage 230 and may display a user list 523 on a display. If a user selects an existing user (e.g., user 1), the processor 130 may recognize the selected existing user as a user from which health information is to be measured. Alternatively, if a user selects a "NEW" button, an input area 524 for inputting user information may be displayed on the user interface 510 as illustrated in FIG. 5D. When the user inputs user information and clicks an "OK" button using the input parts 512 and 513, the processor (e.g., the processor 130 of FIGS. 1 and 2) may register a new user in a user information DB, and may store the measured health information as health information of the new user in the health information DB.

Figure 6A:
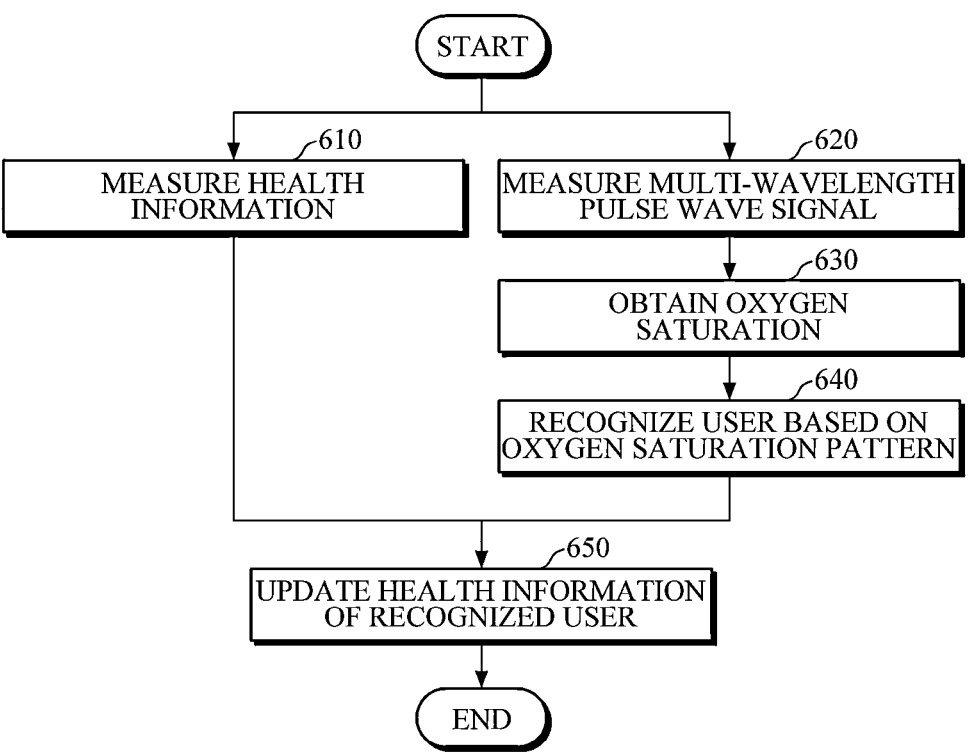
FIG. 6A is a flowchart illustrating a method of user recognition according to an embodiment of the present disclosure.
Figure 6B:
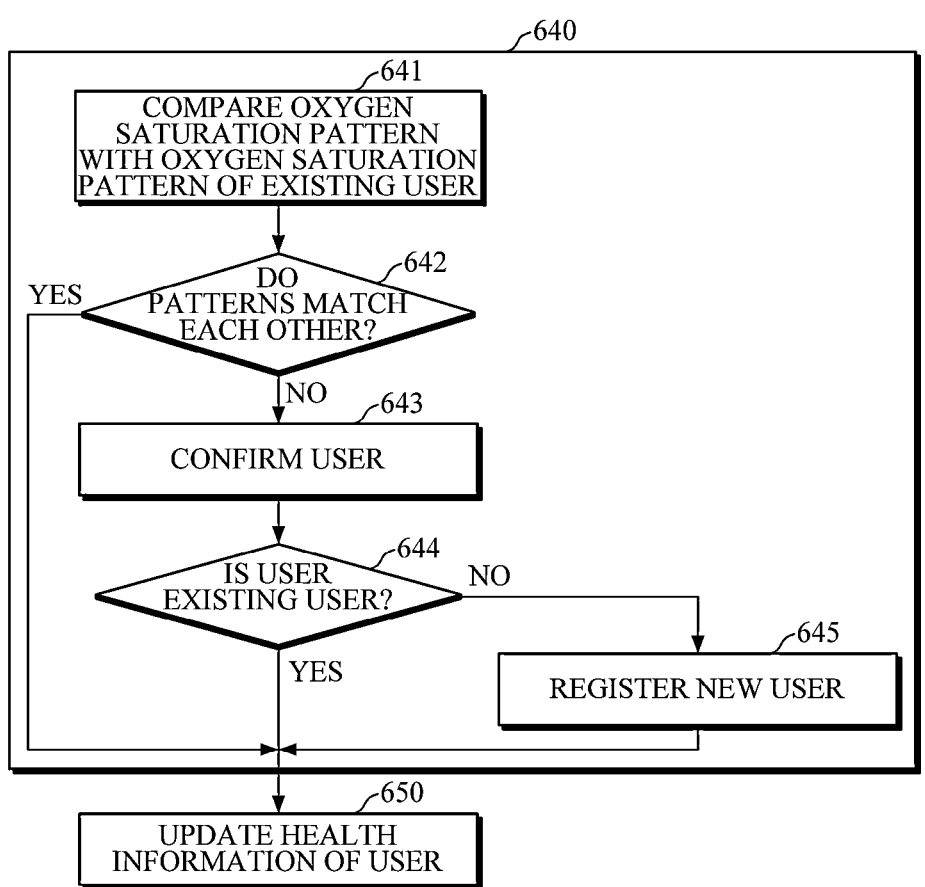

FIG. 6A is a flowchart illustrating a method of user recognition (hereinafter referred to as a user recognition method) according to an embodiment of the present disclosure. FIGS. 6B and 6C are diagrams illustrating examples of a user recognition operation in 640. FIGS. 6A to 6C illustrate an example of a user recognition method performed by the aforementioned user recognition apparatuses 100 and 200, and the method will be briefly described below.

First, the user recognition apparatuses 100 and 200 may measure health information from a user by using the first sensor in operation 610. The health information may include health-related information, such as blood pressure, blood glucose, body fat, body water, body mass, electrocardiogram, heart rate, body temperature, etc., and a user's activity-related information may include a user's amount of exercise, exercise time, walking speed, step count, sleep time, sleep quality, and the like.

In addition, the user recognition apparatuses 100 and 200 may measure a multi-wavelength pulse wave signal in operation 620 from a user, from which the health information is to be measured in operation 610. The multiple wavelengths may include infrared and red wavelengths. The second sensor, including a plurality of channels disposed at different positions, may measure the multi-wavelength pulse wave signal for each channel. The measuring of the health information in 610 and the measuring of the multi-wavelength pulse wave signal in operation 620 may also be performed simultaneously regardless of order.

Then, the user recognition apparatuses 100 and 200 may obtain oxygen saturation in 630 by using the multi-wavelength pulse wave signal measured in operation 620. The user recognition apparatuses 100 and 200 may obtain oxygen saturations for each channel by using the multi-wavelength pulse wave signal of each channel by using the above Equations. The user recognition apparatuses 100 and 200 may obtain oxygen saturations at each time point in a predetermined time period (e.g., five seconds), and may obtain an average of the oxygen saturations at each time point as the oxygen saturation.

Subsequently, in operation 640, the user recognition apparatuses 100 and 200 may recognize the user from whom the health information will be measured based on an oxygen saturation pattern. The user recognition apparatuses 100 and 200 may generate an oxygen saturation pattern map by mapping the oxygen saturations of each channel to their corresponding channel positions in a measurement region of the second sensor, and may recognize the user by using the generated oxygen saturation pattern map.

Referring to FIG. 6B, operation 640 of recognizing the user may include comparing the generated oxygen saturation pattern map of the user with oxygen saturation pattern maps of existing users to determine whether there is a pattern map of an existing user that matches the generated oxygen saturation pattern map in operation 641, and in response to determining that the pattern maps match each other in operation 642, recognizing the matching existing user as the user from which the health information is measured in operation 610. In addition, in response to determining that the pattern maps do not match each other in operation 642, the operation of recognizing the user in operation 640 may include confirming the user in operation 643 by inquiring the user from which the health information is measured in operation 610, determining whether the user is an existing user based on a user input in operation 644, and in response to the user not being the existing user, registering a new user based on user information input by the user in operation 645.

Referring to FIG. 6C, the operation of recognizing the user in 640 may further include, in addition to operations 641 to 645, determining whether to update an oxygen saturation pattern of a recognized existing user in operation 647 in response to there being an existing user of an oxygen saturation pattern that matches the generated oxygen saturation pattern map in operation 642, and in response to determining to update the oxygen saturation pattern, updating the oxygen saturation pattern of the recognized existing user in 648 based on the oxygen saturation of the user which is obtained in operation 630. For example, the oxygen saturation of the existing user may be replaced with an oxygen saturation of a user which is newly obtained in operation 630, or a new oxygen saturation pattern may be generated by obtaining a statistical value (e.g. average) of two oxygen saturations, and the oxygen saturation pattern of the existing user may be replaced with the generated new oxygen saturation pattern.

Then, the health information measured in 610 may be updated in 650 as health information of the user recognized in 640.

Figure 7:
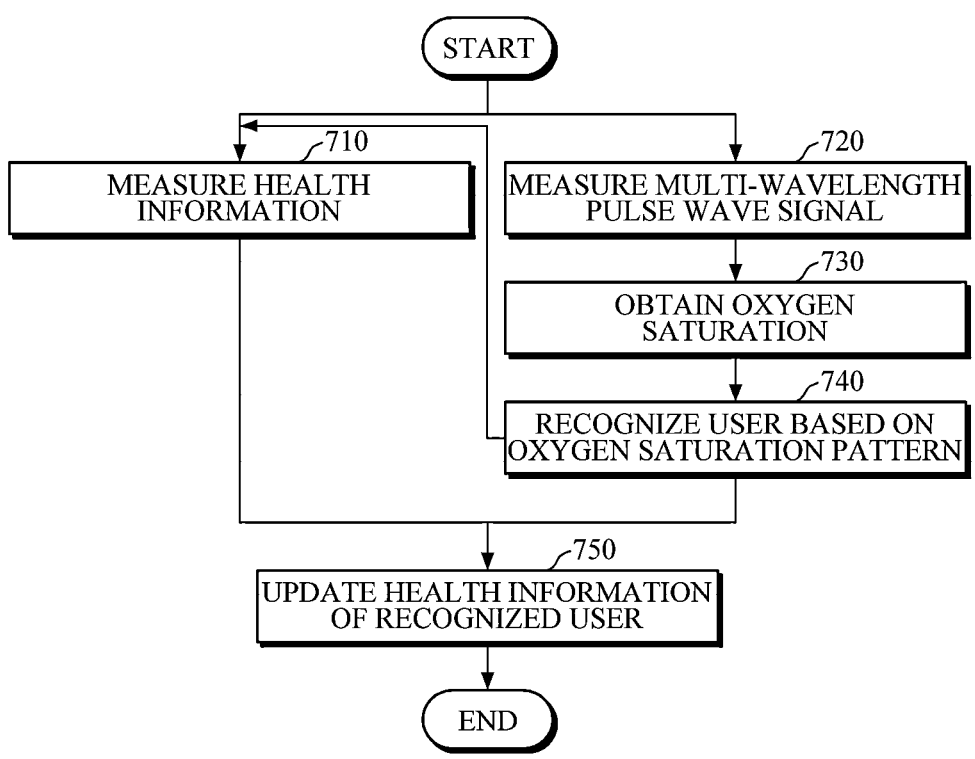
FIG. 7 is a flowchart illustrating a method of user recognition according to another embodiment of the present disclosure.

FIG. 7 is a flowchart illustrating a method of user recognition according to another embodiment of the present disclosure. The method of FIG. 7 is an example of a user recognition method performed by the aforementioned user recognition apparatuses 100 and 200, and will be briefly described below.

The user recognition apparatuses 100 and 200 may measure health information from a user by using the first sensor in operation 710, and while measuring the health information in operation 710, the user recognition apparatuses 100 and 200 may measure a multi-wavelength pulse wave signal from the user in operation 720, may obtain oxygen saturation by using the multi-wavelength pulse wave signal in operation 730, and may recognize a user based on an oxygen saturation pattern in operation 740. In response to recognizing the user in operation 740, the measurement of the health information (e.g., body fat) in operation 710 may be completed by using user information of the recognized user. Then, the user recognition apparatuses 100 and 200 may update, in operation 750, the health information, measured in operation 710, as the health information of the user recognized in operation 740.

Figure 8:
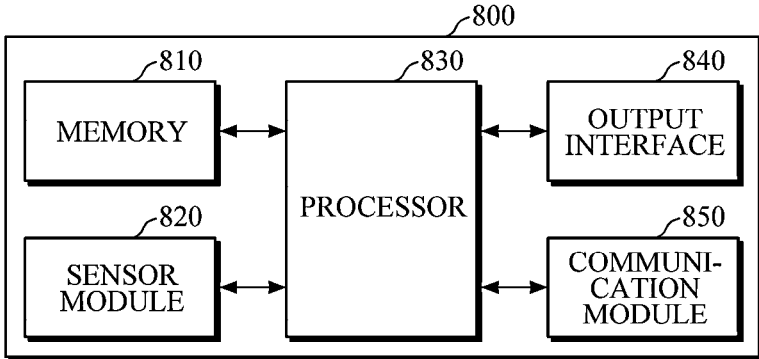
FIG. 8 is a block diagram illustrating an electronic device according to an embodiment of the present disclosure.
Figure 9A:
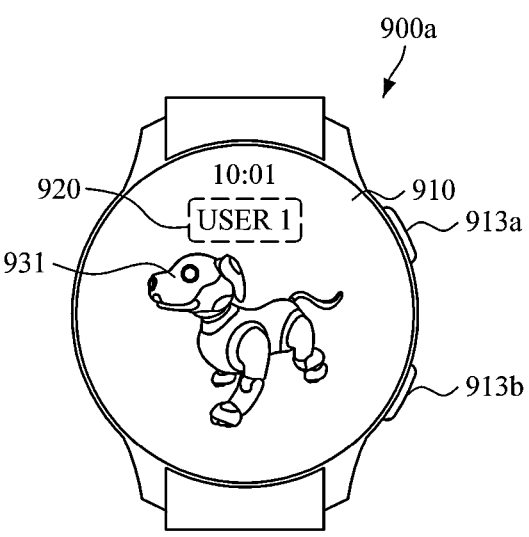
FIGS. 9A and 9B are diagrams explaining an example of a function control operation by user recognition in an electronic device.
Figure 9B:
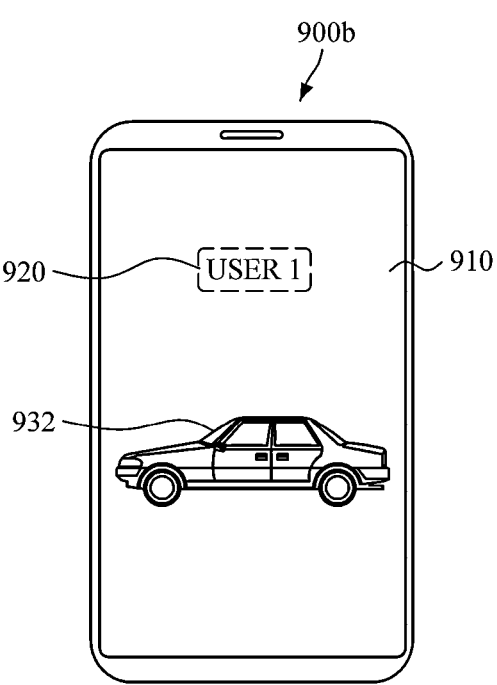

FIG. 8 is a block diagram illustrating an electronic device including the user recognition apparatuses 100 and 200. FIGS. 9A and 9B are diagrams explaining an example of a function control operation by user recognition in an electronic device.

Referring to FIG. 8, an electronic device 800 may include a memory 810, a sensor module 820, a processor 830, an output device 840, and a communication module 850, and may further include various other components not illustrated herein. The electronic device 800 may include the aforementioned user recognition apparatuses 100 and 200. The electronic device 800 may include a smart watch, a smart band, a headband wearable device, an ear-wearable device, a smartphone, a tablet PC, and the like.

The memory 810 may store various data necessary for components (processor 830, sensor module 820, etc.) of the electronic device 800. The data may include, for example, software (programs, etc.), a set of instructions, and input data and/or output data for commands related thereto. The programs may be stored as software in the memory 810 and may include operating system, middleware, and/or application (clock, music, schedule, contact information, message, SNS, drawing, presentation, word processing, spreadsheet, game, phone, video conference, e-mail, web browsing, photo, camera, video, healthcare, user recognition, function control applications, etc.). For example, the data may include a user information DB of users using the electronic device 800, and a health information DB generated for each user in a healthcare application.

The memory 810 may selectively include one or more computer-readable storage media. The computer-readable storage media may store application programs for measuring health information, performing user recognition based on oxygen saturation, health information management based on user recognition, and function control. The memory 830 may selectively include a high-speed random access memory, and a non-volatile memory such as one or more magnetic disk storage devices, flash memory devices, non-volatile solid state memory devices.

The sensor module 820 may detect an operating state (power, temperature, etc.) of the electronic device 800 or an external environmental state (user state, etc.), and may generate an electrical signal and/or data value corresponding to the detected state. The sensor module 820 may include Global Positioning System (GPS), gesture sensor, gyro sensor, barometric pressure sensor, magnetic sensor, acceleration sensor, grip sensor, proximity sensor, color sensor, infrared (IR) sensor, compass sensor, step counter sensor, ultraviolet sensor, 3D touch sensor, biosensor, body temperature sensor, temperature sensor, humidity sensor, and/or illuminance sensor, and the like. At least some of the sensor module 820 may operate as the first sensor or the second sensor of the user recognition apparatus.

The processor 830 may perform a general function (clock, music, photo, etc.), the aforementioned health management function, or a control function of the electronic device 800 or another device connected to the electronic device 800. The control function of the electronic device 800 or another device may include a user authentication function for controlling log-in, executing applications, controlling menus and movement of the device, and the like. Examples of another device connected to the electronic device 800 may include a game console, a robot, a drone, an automobile, TV, a machine (various machines in a smart factory, including components), a mobile device, and an Internet of Things (IoT) device (refrigerator, microwave oven, washing machine, home network, lighting device, cooling and heating device, etc.), a smartphone, a tablet PC, a desktop computer, and the like.

FIG. 9A is a diagram explaining an example of controlling a robot using a smartwatch 900*a*, and FIG. 9B is a diagram explaining an example of controlling a vehicle using a smartphone 900*b*. Upon receiving a request for controlling other device (robot, vehicle), the processor 830 may obtain an oxygen saturation pattern by using a multi-wavelength pulse wave signal measured by the sensor module 820, and may recognize a user by referring to the memory 810. Upon recognizing the user, the processor 830 may determine whether the user is authorized to control the other device, and if the user is authorized, the processor 830 may display a user interface 910 for function control through the output device 840. In this case, a graphic object 920, such as a text message and/or an image, etc., which represents an authorized user (user 1), may be displayed on the user interface 910. In addition, graphic objects 931 and 932, such as a photo, character, and the like of the other device (robot, vehicle), may be displayed on the user interface 910 so that a user may intuitively identify controlling and a control result of the other device, and may change movement and the like of the graphic objects 931 and 932 in synchronization with the control result of the other device.

The output device 840 may include a display device for visually displaying various data (e.g., health information, user recognition, function control, etc.) processed by one or more processors 830. The display device may include a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch.

In addition, the output device 840 may include a sound output device adapted to output sound signals to the outside of the electronic device. The sound output device may include a speaker and/or a receiver. The speaker may be used for general purposes, such as playing multimedia or playing record, and the receiver may be used for incoming calls. The receiver may be implemented separately from, or as part of, the speaker.

Furthermore, the output device 840 may include an audio module adapted to convert a sound into an electrical signal or vice versa. The audio module may obtain the sound via the input device, or may output the sound via the sound output device, and/or a speaker and/or a headphone of another electronic device directly or wirelessly connected to the electronic device 800.

In addition, the output device 840 may include a haptic module adapted to convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The communication module 850 may support establishment of a direct (e.g., wired) communication channel and/or a wireless communication channel between the electronic device 800 and other electronic device within a network environment 200, and performing of communication via the established communication channel. The communication module 850 may include one or more communication processors that are operable independently from the processor 830 and supports a direct communication and/or a wireless communication. When the processor 830 generates a control signal for other device, the communication module 850 may transmit the control signal to the other device, and may receive a control result from the other device and transmit the result to the processor 830.

Figure 10:
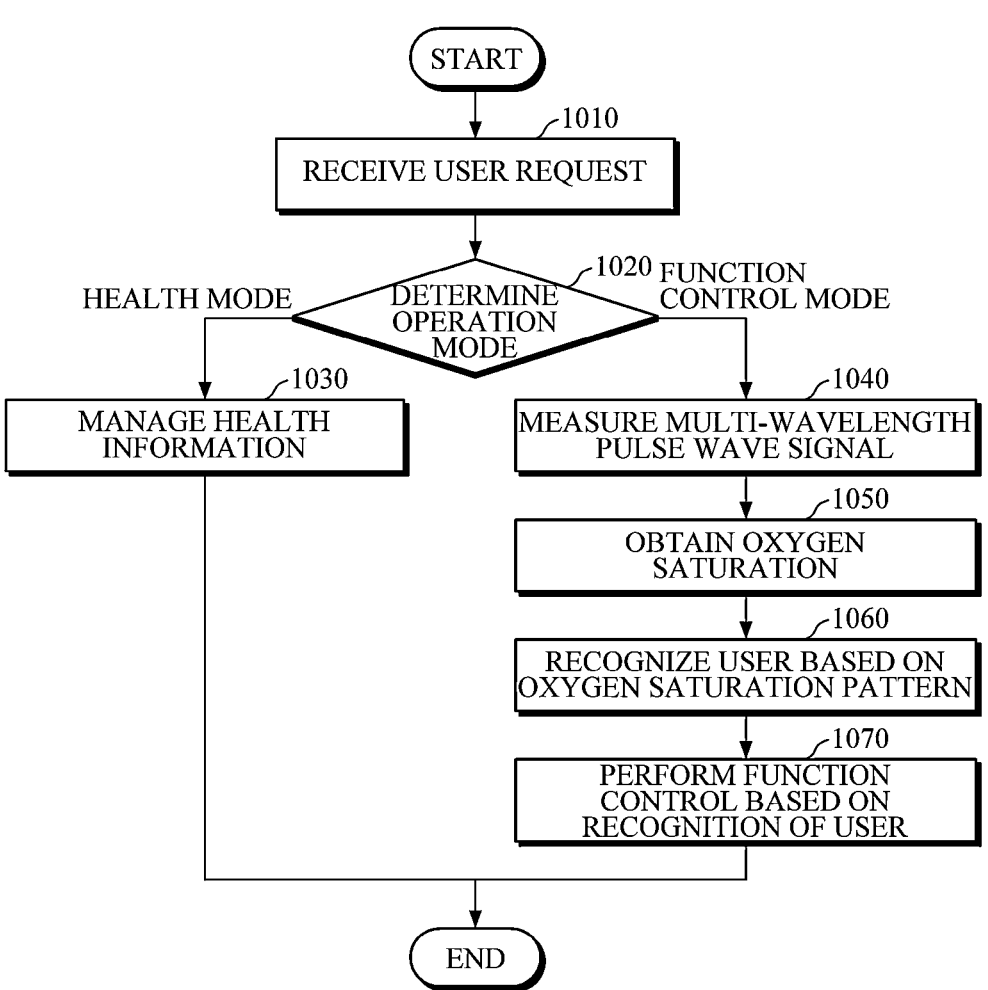
FIG. 10 is a flowchart illustrating an operation method performed by an electronic device according to an embodiment of the present disclosure.

FIG. 10 is a flowchart illustrating an operation method performed by an electronic device according to an embodiment of the present disclosure.

The method of FIG. 10 is an example of a function control method performed by the electronic device 800 of FIG. 8, which is described in detail above, and thus will be briefly described below.

First, upon receiving a user request in operation 1010, the electronic device may determine an operation mode in operation 1020. The operation mode may include a health mode for health management and a function control mode for function control of the apparatus. If the operation mode is the health mode, the electronic device 800 may manage health information in operation 1030 as described above, and if the operation mode is the function control mode, the electronic device 800 may measure a multi-wavelength pulse wave signal by using a sensor module in operation 1040, may obtain oxygen saturation based on the measured multi-wavelength pulse wave signal in operation 1050, may recognize a user based on an oxygen saturation pattern in operation 1060, and may perform function control in operation 1070 if the recognized user is authorized to control a function.

While not restricted thereto. an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs. magnetic tapes. floppy disks. and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for performing user recognition, the apparatus comprising:
   a first sensor configured to measure health information from a user;
   a second sensor configured to measure a pulse wave signal from the user; and
   a processor configured to obtain oxygen saturation based on the pulse wave signal, recognize the user based on an oxygen saturation pattern of the obtained oxygen saturation, and update the measured health information as health information of the recognized user, wherein the second sensor comprises a plurality of channels, wherein each of the plurality of channels has at least one light source and at least one detector, wherein the processor is further configured to calculate the oxygen saturation at each time point in a predetermined period of the pulse wave signal for each channel, and generate the oxygen saturation pattern of the user for each channel based on a statistical value of the oxygen saturation calculated at each time point, and wherein the processor is further configured to generate the oxygen saturation pattern by mapping the oxygen saturations of each channel to their corresponding channel positions in a measurement region of the second sensor.

2. The apparatus of claim 1, wherein the second sensor comprises a light source configured to emit light of multiple wavelengths to skin of the user, and a detector configured to detect the light reflected or scattered from the user.

3. The apparatus of claim 1, further comprising a storage configured to store oxygen saturation patterns of one or more existing users, wherein the processor is further configured to recognize, as the user, an existing user that matches the oxygen saturation pattern of the user among the oxygen saturation patterns of the one or more existing users.

4. The apparatus of claim 3, wherein in response to no oxygen saturation pattern in the storage matching the oxygen saturation pattern of the user, the processor is further configured to recognize the user based on an input of the user.

5. The apparatus of claim 4, wherein in response to the user being a new user, the processor is configured to register the new user in the storage, and store the measured health information as health information of the new user.

6. The apparatus claim 1, wherein the processor is further configured to calculate a similarity between the oxygen saturation pattern of the user and an oxygen saturation pattern of an existing user that is stored in a storage, and in response to the similarity being greater than or equal to a first threshold value, the processor is configured to determine that the oxygen saturation pattern of the user matches the oxygen saturation pattern of the existing user.

7. The apparatus of claim 6, wherein in response to the similarity between the oxygen saturation pattern of the user and the oxygen saturation pattern of the existing user, being greater than or equal to the first threshold value, and being less than or equal to a second threshold value, the processor is further configured to update the oxygen saturation pattern of the existing user based on the oxygen saturation pattern of the user.

8. The apparatus of claim 1, further comprising a storage configured to store user information, including one or more of height, weight, age, gender, and health information of one or more existing users.

9. The apparatus of claim 1, wherein the health information comprises one or more of electrocardiogram, blood glucose, body fat, body mass, blood pressure, heart rate, body temperature, triglyceride, and antioxidant index.

10. A method of performing user recognition, the method comprising:

by a first sensor, measuring health information from a user;

by a second sensor, measuring a pulse wave signal from the user;

obtaining oxygen saturation based on the pulse wave signal;

recognizing the user based on an oxygen saturation pattern of the user; and updating the measured health information as health information of the recognized user, wherein the second sensor comprises a plurality of channels, wherein each of the plurality of channels has at least one light source and at least one detector, wherein the obtaining of the oxygen saturation comprises:

calculating the oxygen saturation at each time point in a predetermined period of the pulse wave signal for each channel; and generating the oxygen saturation pattern of the user for each channel based on a statistical value of the oxygen saturation calculated at each time point, and wherein the generating of the oxygen saturation pattern further comprises generating the oxygen saturation pattern by mapping the oxygen saturations of each channel to their corresponding channel positions in a measurement region of the second sensor.

11. The method of claim 10, wherein the recognizing of the user comprises recognizing, as the user, an existing user that matches the oxygen saturation pattern of the user, among oxygen saturation patterns of one or more existing users which are stored in a storage.

12. The method of claim 11, wherein the recognizing of the user comprises, in response to no oxygen saturation pattern in the storage matching the oxygen saturation pattern of the user, recognizing the user based on an input of the user.

13. The method of claim 12, further comprising, in response to the user being a new user, registering the new user in the storage, wherein the updating of the measured health information comprises storing the measured health information as health information of the new user.

14. The method of claim 10, wherein the recognizing of the user comprises:

calculating a similarity between the oxygen saturation pattern of the user and an oxygen saturation pattern of an existing user; and in response to the similarity being greater than or equal to a first threshold value, determining that the oxygen saturation pattern of the user matches the oxygen saturation pattern of the existing user.

15. The method of claim 14, wherein the recognizing of the user comprises, in response to the similarity between the oxygen saturation pattern of the user and the oxygen saturation pattern of the existing user being greater than or equal to the first threshold value, and being less than or equal to a second threshold value, updating the oxygen saturation pattern of the existing user based on the oxygen saturation pattern of the user.

16. The method of claim 10, further comprising extracting user information of the recognized user from a storage, wherein the measuring of the health information comprises obtaining the health information based on the extracted user information.

* * * * *